United States Patent [19]

Martin

[11] Patent Number: 5,512,273

[45] Date of Patent: Apr. 30, 1996

[54] TOP NAIL COAT COMPOSITION

[75] Inventor: Frederick L. Martin, St. John, Ind.

[73] Assignee: Almell, Ltd., Dallas, Tex.

[21] Appl. No.: 332,539

[22] Filed: Oct. 31, 1994

[51] Int. Cl.⁶ ............................ A61K 7/04; A61K 7/043
[52] U.S. Cl. ........................................ 424/61; 424/78.03
[58] Field of Search ........................ 424/61, 401, 78.03

[56] References Cited

U.S. PATENT DOCUMENTS

| | | | |
|---|---|---|---|
| 2,173,755 | 5/1936 | Fuller | 167/85 |
| 2,824,098 | 2/1958 | Volberg et al. | 260/230 |
| 4,097,589 | 6/1978 | Shansky | 424/61 |
| 4,179,304 | 12/1979 | Rossomando | 106/177 |
| 4,229,227 | 10/1980 | Ikeda et al. | 106/181 |
| 4,301,046 | 11/1981 | Schlossman | 260/16 |
| 4,409,203 | 10/1983 | Gordon | 424/61 |
| 4,421,881 | 12/1983 | Benkendorf et al. | 524/24 |
| 4,649,045 | 3/1987 | Gaske et al. | 424/61 |
| 4,712,571 | 12/1987 | Remz et al. | 132/88.7 |
| 4,740,370 | 4/1988 | Faryniarz et al. | 424/61 |
| 4,747,419 | 5/1988 | Flynn et al. | 132/73 |
| 4,749,564 | 6/1988 | Faryniarz et al. | 424/61 |
| 4,798,720 | 1/1989 | Holder | 424/61 |
| 4,820,509 | 4/1989 | Yamazaki et al. | 424/61 |
| 4,897,261 | 1/1990 | Yamazaki et al. | 424/61 |
| 5,071,639 | 12/1991 | Soyama | 424/61 |
| 5,102,659 | 4/1992 | Castrogiovanni | 424/61 |
| 5,130,125 | 7/1992 | Martin | 424/61 |
| 5,206,111 | 4/1993 | Pappas | 424/61 |

*Primary Examiner*—Thurman K. Page
*Assistant Examiner*—Sally Gardner
*Attorney, Agent, or Firm*—Richards, Medlock & Andrews

[57] ABSTRACT

A top coat nail polish composition, which is at least substantially free of aromatic solvents, contains at least one cellulose ester, a mixture of aliphatic and cycloaliphatic solvents for the cellulose ester, a plasticizer for the cellulose ester, at least two UV blocking agents having different effective UV wavelength blockage ranges, a smoothing agent, an adhesion promoter, and an alkanol solvent for the smoothing agent and the adhesion promoter.

17 Claims, No Drawings

TOP NAIL COAT COMPOSITION

FIELD OF THE INVENTION

The invention relates to a composition for a top coat which can be applied over a coating of nail polish on nails.

BACKGROUND OF THE INVENTION

Nail polish is generally applied to fingernails or toe nails as two or more layers, for example in the form of a base coat layer, one or more pigmented layers, and a top coat. It is generally desirable for each applied coat to be dry before the application of the next coat. However, such drying time substantially increases the total time required for a multi-coat application. It is also desirable that the last coat dry relatively quickly so that the wearer is free to engage in other activities promptly after completing the application of the last coat. However, if the exterior surface of the top coat dries too fast, solvents can be trapped at the interface between the top coat and the previously applied undercoat, reducing the cohesiveness of the previously applied undercoat and the adherence of the top coat to the previously applied undercoat.

Fuller, U.S. Pat. No. 2,173,755 discloses a nail enamel which spreads easily and dries within one and a half minutes to produce a single layer of a non-tacky, durable film, which is readily removable by ethyl acetate and butyl acetate. The Fuller composition utilized non-explosive esters of cellulose dissolved in organic solvents, e.g. ethyl cellulose or cellulose aceto butyrate dissolved in ethylene dichloride, as a replacement for the previously employed nitrocotton, which is explosive. Fuller used diethylene dioxide as a solvent for resins and plasticizers which were to be added to the cellulose ester/organic solvent mixture.

Rossomando, U.S. Pat. No. 4,179,304, discloses the use of a nail polish composition comprising sucrose acetate isobutyrate, a resin selected from sucrose benzoate and sucrose benzoate with polymeric methyl methacrylate, and a plasticizer selected from organic phthalates, organic adipates and organic phosphates, e.g. butyl benzyl phthalate. An objective of the Rossomando composition was to avoid the use of carcinogenic formaldehyde containing resins which had been previously employed in nail polish compositions. Rossomando also discloses that film forming resins such as nitrocellulose, cellulose propionate, cellulose acetate butyrate, ethyl cellulose and acrylic resins could be blended into his nail polish composition. Rossomando discloses the use of a combination of ethyl acetate, butyl acetate and toluene as the solvents for the isopropyl wet nitrocellulose in the basic composition of his working examples.

Martin et al, U.S. Pat. No. 5,130,125, discloses a nail polish top coat composition for application over wet nail polish which dries quickly to a non-tacky, non-brittle solid coat. The preferred composition is set forth in Example 1 of U.S. Pat. No. 5,130,125 as containing toluene, n-butyl acetate, cellulose acetate butyrate ester 318, cellulose acetate butyrate ester 551, benzophenone-1, butyl benzyl phthalate, polysiloxane copolymer, and isopropyl alcohol. While this Martin et al top coat has many advantages, the use of toluene is considered to be undesirable because it is toxic by ingestion, inhalation, or skin absorption, and may cause mild macrocytic anemia. Accordingly, there is a need for a top nail coat composition which is at least substantially free of aromatic solvents such as toluene.

Also, while the benzophenone-1 in the Martin et al top coat composition is a good UV blocking agent, it does not provide the desired level of UV blocking for the full range of ultraviolet radiation. Accordingly, there is a need for a top nail coat composition which has an enhanced range of UV blockage. Similarly, while the polysiloxane copolymer of the Martin et al composition reduces friction, improves the flow of the top coat composition during application, and improves the levelness and gloss of the surface of the top coat composition upon drying, the adhesion of the top coat to the previously applied coats is not as strong as is desired.

SUMMARY OF THE INVENTION

A top coat composition in accordance with the present invention is at least substantially free of aromatic solvents and comprises one or more cellulose esters and a mixture of aliphatic and cycloaliphatic solvents for the cellulose esters.

In a presently preferred composition, the cellulose ester comprises one or more cellulose acetate butyrate esters, and the composition includes a plasticizer for the cellulose esters, at least two UV blocking agents having different effective UV wavelength blockage ranges, a smoothing agent and an adhesion promoter.

DETAILED DESCRIPTION OF THE INVENTION

The cellulose esters which can be employed in the invention as a film forming resin include cellulose esters containing monocarboxylic acid groups of 2 to 4 carbon atoms, for example, cellulose acetate, cellulose propionate, cellulose butyrate, cellulose acetate butyrate esters, cellulose isobutyrate, and mixtures of any two or more thereof. The presently preferred cellulose esters are the cellulose acetate butyrate esters.

The solvent for the cellulose esters is a mixture of acyclic aliphatic and cycloaliphatic solvents. Suitable aliphatic solvents include alkanes having 4 to 6 carbon atoms, aliphatic esters having 3 to 6 carbon atoms, alkanols having 2 to 6 carbon atoms, e.g. n-butane, isobutane, n-pentane, isopentane, hexane, methyl propionate, methyl acetate, ethyl acetate, n-propyl acetate, n-butyl acetate, n-propyl formate, ethyl propionate, ethanol, n-propanol, isopropanol, n-butanol, n-pentanol, n-hexanol, and mixtures of any two or more thereof. Suitable cycloaliphatic solvents include cycloalkanes having 4 to 6 carbon atoms, cycloaliphatic esters having 4 to 6 carbon atoms, cycloalkanols having 4 to 6 carbon atoms, e.g. cyclobutane, cyclopentane, cyclohexane, cyclobutylcarbinol, naphthenes, and mixtures of any two or more thereof.

In general, the cycloaliphatic solvents will constitute from about 1 to about 20 vol. %, preferably from about 2 to about 15 vol. %, and more preferably from about 3 to about 10 vol. % of the mixture of solvents used to dissolve the cellulose esters. A presently preferred solvent mixture for the cellulose esters comprises about 30 to about 45 vol. % ethyl acetate, about 40 to about 65 vol. % n-butyl acetate, and about 5 to about 20 vol. % Naphtholite™ naphthenic material. The Naphtholite™ naphthenic material is a naphthenic material available from Union 76 Chemicals as a mixture of paraffins and cycloparaffins containing less than 1 percent aromatics, with the paraffin content being in the range of about 37 to about 50 percent and the cycloparaffin content being in the range of about 62 to about 49 percent.

The ratio of the cellulose ester solvent mixture to the cellulose esters can be any suitable value, but in general will be in the range of about 10 to about 25 fluid ounces of the solvent mixture per 100 grams of cellulose ester, and preferably will be in the range of about 12 to about 16 fluid ounces of the solvent mixture per 100 grams of cellulose ester.

Any suitable plasticizer for the cellulose esters can be employed in the present top coat composition. Examples include organic phthalates, organic adipates, and organic phosphates, e.g. butyl benzyl phthalate, camphor, dibutyl phthalate, tricresyl phosphate, diethyl phthalate, tributyl phosphate, dibutyl glycolate, dioctyl phthalate, butyl stearate, and mixtures of any two or more thereof. The plasticizer can be employed in any suitable amount, but will in general be employed in an amount in the range of about 0.1 to about 5 fluid ounces per 100 grams of cellulose ester, and preferably will be in the range of about 0.2 to about 1 fluid ounce per 100 grams of cellulose ester.

Any suitable UV blocker can be employed in the present top coat composition. However, it is presently preferred to employ at least two UV blockers having different ranges of UV wavelength blockage so as to extend the protection against UV radiation. Any suitable amount of the UV blockers can be employed, but the total amount of UV blockers will generally be in the range of about 0.1 to about 5 grams per 100 grams of cellulose ester, and preferably will be in the range of about 0.2 to about 1 gram per 100 grams of cellulose ester. The presently preferred UV blockers are benzophenone-1 and benzophenone-3, with the amount of the benzophenone-1 preferably being in the range of about 0.5 to about 0.8 gram per 100 grams of cellulose ester, and the amount of the benzophenone-3 preferably being in the range of about 0.001 to about 0.002 gram per 100 grams of cellulose ester.

In order to provide the desired characteristics of flow and level, the top coat composition can contain a smoothing agent. The smoothing agent reduces friction, improves the flow of the top coat composition during application, and improves the levelness and gloss of the surface of the top coat composition upon drying. Suitable smoothing agents include silicone polymers and copolymers, polyamides, polyacrylamides, and polycarboxylic acids, and mixtures of any two or more thereof. Any suitable amount of smoothing agent can be employed, but the amount will generally be in the range of 0 to about 5 grams per 100 grams of cellulose ester, and preferably will be in the range of about 0.5 to about 3 grams per 100 grams of cellulose ester. The presently preferred smoothing agent is a polysiloxane copolymer.

In order to provide the desired characteristics of adhesion, the top coat composition can contain an adhesion promoter. The adhesion promotor improves the adhesion of the top coat to the previously applied coats. Any suitable amount of adhesion promoter can be employed, but the amount will generally be in the range of 0 to about 5 grams per 100 grams of cellulose ester, and preferably will be in the range of about 0.2 to about 2 grams per 100 grams of cellulose ester. Examples of suitable adhesion promoters which can be employed include sucrose benzoates, sucrose acetate isobutyrates, and aminoalkoxysilanes, with aminomethoxysilane being presently preferred.

In order to facilitate the introduction of the smoothing agent and the adhesion promotor into the top coat composition, it is desirable that these components first be dispersed in a suitable solvent, preferably an alkanol having 2 to 6 carbon atoms, and the resulting solution then be added to the solution of the cellulose ester in its mixture of solvents. The solvent for the smoothing agent and the adhesion promotor can be employed in any suitable amount, but will in general be employed in an amount in the range of about 0.5 to about 5 fluid ounces per 100 grams of cellulose ester, and preferably will be in the range of about 1 to about 3 fluid ounces per 100 grams of cellulose ester. The presently preferred solvent for the smoothing agent and the adhesion promotor is isopropyl alcohol.

In general, the cycloaliphatic solvents will constitute from about 0.9 to about 18 vol. %, preferably from about 1.8 to about 13.5 vol. %, and more preferably from about 2.7 to about 9 vol. % of the total amount of solvents in the top coat composition, including the alkanol employed to dissolve the smoothing agent and the adhesion promotor.

EXAMPLE I

A top nail coat composition, not containing any cycloparaffins, was prepared with the following ingredients:

| INGREDIENT | AMOUNT |
| --- | --- |
| Ethyl acetate | 40.0 fluid oz. |
| N-butyl acetate | 48.0 fluid oz. |
| Cellulose acetate butyrate ester 381 | 560 grams |
| Cellulose acetate butyrate ester 551 | 80 grams |
| Benzophenone-1 | 4 grams |
| Benzophenone-3 | 0.01 gram |
| Butyl benzyl phthalate | 4.0 fluid oz. |
| Polysiloxane copolymer | 12 grams |
| Aminomethoxysilane | 1 gram |
| Isopropyl alcohol | 10.0 fluid oz. |

The ethyl acetate and the n-butyl acetate were blended, and then the cellulose acetate butyrate esters were sifted into the blend of the acetate solvents while the resulting mixture was stirred at slow speed in order to avoid agglomeration of the esters. The resulting mixture was then stirred at high speed until the esters had dissolved in the solvent blend. The polysiloxane copolymer, the aminomethoxysilane, and the isopropyl alcohol were admixed together and the resulting admixture was then added to the solution of the cellulose esters in the solvent mixture along with the benzophenone-1, benzophenone-3, and the butyl benzyl phthalate, while the resulting combination was stirred at low speed.

The resulting composition was applied as a top coat over a wet undercoat of nail polish. The exterior surface of the top coat dried in approximately 60 seconds, but the adhesion of the top coat to the undercoat was considered to be inadequate even though the top coat composition contained an adhesion promotor. The problem was considered to have resulted from the presence of a significant amount of solvent at the interface of the top coat and the undercoat when the exterior surface of the top coat was considered dry.

EXAMPLE II

A top nail coat composition, containing cycloparaffins and being at least substantially free of aromatic solvents, was prepared with the following ingredients:

| INGREDIENT | AMOUNT |
| --- | --- |
| Ethyl acetate | 30.0 fluid oz. |
| N-butyl acetate | 48.0 fluid oz. |
| Naphtholite 66/3 | 10.0 fluid oz. |
| Cellulose acetate butyrate ester 381 | 560 grams |
| Cellulose acetate butyrate ester 551 | 80 grams |
| Benzophenone-1 | 4 grams |
| Benzophenone-3 | 0.01 gram |
| Butyl benzyl phthalate | 4.0 fluid oz. |
| Polysiloxane copolymer | 12 grams |
| Aminomethoxysilane | 1 gram |
| Isopropyl alcohol | 10.0 fluid oz. |

The Naphtholite™ 66/3 is a mixture of approximately 37 wt % acyclic paraffins, approximately 62 wt % cycloparaffins, and less than 1% aromatics, and has a flash point of 12.2° C. an initial boiling point of 249° C., and a vapor pressure of 14 mm Hg at 20° C.

The resulting composition was applied as a top coat over a wet undercoat of nail polish. The exterior surface of the top coat dried in approximately 75 seconds, and the adhesion of the top coat to the undercoat was considered to be adequate. Thus, while the presence of the cycloparaffins slightly increased the drying time of the top coat, the drying time was still acceptable, and this permitted the concentration of solvents at the interface of the top coat and the undercoat to be reduced sufficiently so that adequate adhesion of the top coat to the undercoat was achieved.

Reasonable variations in and modifications to the invention are possible within the scope of the foregoing description and the appended claims.

That which is claimed:

1. A composition comprising:

at least one cellulose ester containing monocarboxylic acid groups having from 2 to 4 carbon atoms, and solvent for said at least one cellulose ester, said solvent consisting essentially of a mixture of at least one aliphatic solvent for said at least one cellulose ester and at least one cycloaliphatic solvent for said at least one cellulose ester, the composition being at least substantially free of aromatic solvents;

wherein said at least one aliphatic solvent for said at least one cellulose ester is selected from the group consisting of alkanes having 4 to 6 carbon atoms, aliphatic esters having 3 to 6 carbon atoms, and alkanols having 2 to 6 carbon atoms;

wherein said at least one cycloaliphatic solvent for said at least one cellulose ester is selected from the group consisting of cycloalkanes having 4 to 6 carbon atoms, cycloaliphatic esters having 4 to 6 carbon atoms, and cycloalkanols having 4 to 6 carbon atoms;

wherein said at least one cycloaliphatic solvent constitutes from about 1 to about 20 volume percent of said mixture;

wherein said mixture comprises about 30 to about 45 volume percent ethyl acetate, about 40 to about 65 volume percent n-butyl acetate, and about 5 to about 20 volume percent naphthenic material, and wherein said naphthenic material is a mixture of acyclic paraffins and cycloparaffins containing less than 1 percent aromatics.

2. A composition in accordance with claim 1 wherein said at least one cellulose ester comprises at least one cellulose acetate butyrate ester.

3. A composition in accordance with claim 1 wherein said at least one cycloaliphatic solvent constitutes about 2 to about 15 volume percent of said mixture.

4. A composition in accordance with claim 1 wherein said at least one cycloaliphatic solvent constitutes about 3 to about 10 volume percent of said mixture.

5. A composition in accordance with claim 1 wherein said naphthenic material comprises about 37 to about 50 percent acyclic paraffins, about 62 to about 49 percent cycloparaffins, and less than 1 percent aromatics.

6. A composition in accordance with claim 1 wherein said naphthenic material comprises about 37 percent acyclic paraffins, about 62 percent cycloparaffins, and less than 1 percent aromatics.

7. A composition in accordance with claim 1 wherein said at least one cycloaliphatic solvent constitutes from about 0.9 to about 18 volume percent of the total amount of solvents in the composition.

8. A composition in accordance with claim 7, further comprising a smoothing agent and an adhesion promotor, wherein said smoothing agent improves levelness and gloss of a surface of the top coat nail polish composition upon drying, and wherein said adhesion promotor improves adhesion of the top coat nail polish composition to any previously applied coats.

9. A top coat nail polish composition comprising:

at least one cellulose acetate butyrate ester, solvent for said at least one cellulose acetate butyrate ester, said solvent consisting essentially of a mixture of at least one aliphatic solvent for said at least one cellulose acetate butyrate ester and at least one cycloaliphatic solvent for said at least one cellulose acetate butyrate ester, wherein said at least one aliphatic solvent for the cellulose ester is selected from the group consisting of alkanes having 4 to 6 carbon atoms, aliphatic esters having 3 to 6 carbon atoms, and alkanols having 2 to 6 carbon atoms, wherein said at least one cycloaliphatic solvent for the cellulose ester is selected from the group consisting of cycloalkanes having 4 to 6 carbon atoms, cycloaliphatic esters having 4 to 6 carbon atoms, and cycloalkanols having 4 to 6 carbon atoms, and wherein said at least one cycloaliphatic solvent constitutes from about 1 to about 20 volume percent of said mixture, a plasticizer for said at least one cellulose acetate butyrate ester, and at least one UV blocking agent, the top coat nail polish composition being at least substantially free of aromatic solvents, wherein said mixture comprises about 30 to about 45 volume percent ethyl acetate, about 40 to about 65 volume percent n-butyl acetate, and about 5 to about 20 volume percent naphthenic material, and wherein said naphthenic material is a mixture of acyclic paraffins and cycloparaffins containing less than 1 percent aromatics.

10. A composition in accordance with claim 9 wherein said naphthenic material comprises about 37 to about 50 percent acyclic paraffins, about 62 to about 49 percent cycloparaffins, and less than 1 percent aromatics.

11. A composition in accordance with claim 10, wherein said at least one UV blocking agent comprises at least two UV blocking agents having effective UV wavelength blockage ranges which are different from each other.

12. A composition consisting essentially of the following:

| INGREDIENT | AMOUNT |
| --- | --- |
| Ethyl acetate | 30.0 fluid oz. |
| N-butyl acetate | 48.0 fluid oz. |
| Naphthenic material | 10.0 fluid oz. |
| Cellulose acetate butyrate ester 381 | 560 grams |
| Cellulose acetate butyrate ester 551 | 80 grams |
| Benzophenone-1 | 4 grams |
| Benzophenone-3 | 0.01 gram |
| Butyl benzyl phthalate | 4.0 fluid oz. |
| Polysiloxane copolymer | 12 grams |
| Aminomethoxysilane | 1 gram |
| Isopropyl alcohol | 10.0 fluid oz. | wherein said naphthenic material is a mixture of acyclic paraffins and cycloparaffins containing less than 1 percent aromatics.

13. A method for making a top coat nail polish composition comprising at least one cellulose ester containing monocarboxylic acid groups having 2 to 4 carbon atoms, and solvent, wherein said solvent consists essentially of a mixture of at least one aliphatic solvent and at least one cycloaliphatic solvent and wherein said top coat nail polish composition is at least substantially free of aromatic solvents, said method comprising:

forming a mixed solvent, said mixed solvent consisting essentially of a mixture of at least one aliphatic solvent and at least one cycloaliphatic solvent;

wherein each said at least one aliphatic solvent is selected from the group consisting of alkanes having 4 to 6 carbon atoms, aliphatic esters having 3 to 6 carbon atoms, and alkanols having 2 to 6 carbon atoms;

wherein each said at least one cycloaliphatic solvent is selected from the group consisting of cycloalkanes having 4 to 6 carbon atoms, cycloaliphatic esters having 4 to 6 carbon atoms, and cycloalkanols having 4 to 6 carbon atoms; and wherein said at least one cycloaliphatic solvent constitutes from about 1 to about 20 volume percent of said mixed solvent;

dissolving at least one cellulose ester in said mixed solvent to form a first solution;

wherein said at least one cellulose ester comprises at least one cellulose acetate butyrate ester;

adding to said first solution at least one plasticizer for said at least one cellulose ester and at least two UV blocking agents having effective UV wavelength blockage ranges which are different from each other;

mixing a smoothing agent and an adhesion promotor with a suitable alkanol having 2 to 6 carbon atoms to form a second solution;

wherein said smoothing agent improves levelness and gloss of a surface of the top coat nail polish composition upon drying;

wherein said adhesion promotor improves adhesion of the top coat nail polish composition to any previously applied coats;

wherein said suitable alkanol is suitable to facilitate introduction of said smoothing agent and said adhesion promotor into the top coat nail polish composition; and combining said second solution and said first solution containing the thus added at least one plasticizer and the thus added at least two UV blocking agents, wherein said mixture comprises about 30 to about 45 volume percent ethyl acetate, about 40 to about 65 volume percent n-butyl acetate, and about 5 to about 20 volume percent naphthenic material; and wherein said naphthenic material is a mixture of acyclic paraffins and cycloparaffins containing less than 1 percent aromatics.

14. A method in accordance with claim 13 wherein said at least one cycloaliphatic solvent constitutes from about 0.9 to about 18 volume percent of the total amount of solvents in the top coat nail polish composition.

15. A method in accordance with claim 13 wherein said naphthenic material comprises about 37 to about 50 percent acyclic paraffins, about 62 to about 49 percent cycloparaffins, and less than 1 percent aromatics.

16. A method in accordance with claim 15, wherein said at least one plasticizer comprises butyl benzyl phthalate, and wherein said at least two UV blocking agents comprise benzophenone-1 and benzophenone-3.

17. A method in accordance with claim 16, wherein said smoothing agent comprises a polysiloxane copolymer, wherein said adhesion promotor comprises aminomethoxysilane, wherein said suitable alkanol comprises isopropyl alcohol, and wherein said cycloaliphatic solvent constitutes from about 0.9 to about 18 volume percent of the total amount of solvents in the top coat nail polish composition.

* * * * *